(12) United States Patent
Belisle et al.

(10) Patent No.: US 12,194,432 B2
(45) Date of Patent: *Jan. 14, 2025

(54) CHROMATOGRAPHY RESIN HAVING AN ANIONIC EXCHANGE-HYDROPHOBIC MIXED MODE LIGAND

(71) Applicant: BIO-RAD LABORATORIES, INC., Hercules, CA (US)

(72) Inventors: Christopher Belisle, Walnut Creek, CA (US); Hong Chen, San Ramon, CA (US); Yueping Xu, Albany, CA (US); Jiali Liao, San Ramon, CA (US); Xuemei He, Walnut Creek, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,991

(22) Filed: Apr. 27, 2023

(65) Prior Publication Data
US 2023/0264171 A1     Aug. 24, 2023

Related U.S. Application Data

(63) Continuation of application No. 16/967,429, filed as application No. PCT/US2019/016619 on Feb. 5, 2019, now Pat. No. 11,666,888.

(60) Provisional application No. 62/626,245, filed on Feb. 5, 2018.

(51) Int. Cl.
| | | |
|---|---|---|
| *B01D 15/32* | (2006.01) |
| *B01D 15/36* | (2006.01) |
| *B01D 15/38* | (2006.01) |
| *B01J 20/26* | (2006.01) |
| *B01J 20/289* | (2006.01) |
| *B01J 20/32* | (2006.01) |
| *C07K 16/06* | (2006.01) |

(52) U.S. Cl.
CPC .......... *B01J 20/262* (2013.01); *B01D 15/363* (2013.01); *B01J 20/289* (2013.01); *B01J 20/3208* (2013.01); *B01J 20/3219* (2013.01); *B01J 20/3227* (2013.01); *B01J 20/3248* (2013.01); *B01J 20/3253* (2013.01); *B01J 20/3285* (2013.01); *C07K 16/065* (2013.01); *B01D 15/327* (2013.01); *B01D 15/3847* (2013.01)

(58) Field of Classification Search
CPC .... B01J 20/262; B01J 20/289; B01J 20/3208; B01J 20/3219; B01J 20/3227; B01J 20/3248; B01J 20/3253; B01J 20/3285; B01D 15/363; B01D 15/327; B01D 15/3847; C07K 16/065
See application file for complete search history.

(56) References Cited

U.S. PATENT DOCUMENTS

| | | | |
|---|---|---|---|
| 4,341,720 A | 7/1982 | Vogel et al. |
| 4,837,348 A | 6/1989 | Stolowitz et al. |
| 5,463,011 A | 10/1995 | Brown et al. |
| 5,681,838 A | 10/1997 | Zoller et al. |
| 6,300,498 B1 | 10/2001 | Tanaka et al. |
| 6,498,236 B1 | 12/2002 | Lihme et al. |
| 7,049,460 B1 | 5/2006 | Magdolen et al. |
| 7,208,521 B2 | 4/2007 | Magdolen et al. |
| 7,265,220 B2 | 9/2007 | De Nanteuil et al. |
| 7,288,654 B2 | 10/2007 | Shiraishi et al. |
| 7,655,793 B2 | 2/2010 | Herzer et al. |
| 7,714,112 B2 | 5/2010 | Engstrand et al. |
| 7,867,784 B2 | 1/2011 | Engstrand et al. |
| 7,932,281 B2 | 4/2011 | Saitou et al. |
| 7,960,459 B2 | 6/2011 | Noro et al. |
| 8,853,309 B2 | 10/2014 | Yano et al. |
| 8,895,710 B2 | 11/2014 | Engstrand et al. |
| 9,309,282 B2 | 4/2016 | Liao et al. |
| 9,669,402 B2 | 6/2017 | Liao et al. |
| 9,777,436 B2 | 10/2017 | Ringold et al. |
| 2006/0079543 A1 | 4/2006 | Sum et al. |
| 2006/0160864 A1 | 7/2006 | Shiraishi et al. |
| 2006/0178359 A1 | 8/2006 | Shiraishi et al. |
| 2008/0311681 A1 | 12/2008 | Johannsen et al. |
| 2009/0029994 A1 | 1/2009 | Nakamura et al. |
| 2009/0098086 A1 | 4/2009 | Zask et al. |
| 2009/0182091 A1 | 7/2009 | Noro et al. |
| 2010/0160332 A1 | 6/2010 | Rozas Hernando et al. |
| 2011/0135650 A1 | 6/2011 | Chackalamannil et al. |
| 2011/0224155 A1 | 9/2011 | Tachdjian et al. |
| 2012/0178772 A1 | 7/2012 | Jenkins |
| 2012/0178773 A1 | 7/2012 | Jenkins |
| 2013/0237692 A1 | 9/2013 | Liao et al. |
| 2015/0069342 A1 | 3/2015 | Lee et al. |
| 2015/0069344 A1 | 3/2015 | Kim et al. |

(Continued)

FOREIGN PATENT DOCUMENTS

| | | |
|---|---|---|
| CA | 2607992 | 2/2003 |
| CN | 103450112 | 12/2013 |

(Continued)

OTHER PUBLICATIONS

Chen, Z. et al. "Insights in understanding aggregate formation and dissociation in cation exchange chromatography for a structurally unstable Fc-fusion protein" *Journal of Chromatography A*, 2016, pp. 110-122, vol. 1460.

(Continued)

*Primary Examiner* — Benjamin L Lebron

(74) *Attorney, Agent, or Firm* — SALIWANCHIK, LLOYD & EISENSCHENK

(57) ABSTRACT

Chromatography resins having mixed mode ligands and methods of using such resins are provided.

28 Claims, No Drawings

(56) References Cited

U.S. PATENT DOCUMENTS

| | | | |
|---|---|---|---|
| 2015/0069347 A1 | 3/2015 | Kim et al. |
| 2015/0069355 A1 | 3/2015 | Hwang et al. |
| 2015/0073128 A1 | 3/2015 | Engstrand et al. |
| 2015/0258539 A1 | 9/2015 | Cramer et al. |
| 2015/0299248 A1 | 10/2015 | Maloisel et al. |
| 2016/0244606 A1 | 8/2016 | Ravichandran et al. |
| 2016/0329501 A1 | 11/2016 | Kim et al. |
| 2017/0040121 A1 | 2/2017 | Satou et al. |
| 2017/0073331 A1 | 3/2017 | Kim et al. |
| 2017/0232433 A1 | 8/2017 | Liao et al. |

FOREIGN PATENT DOCUMENTS

| | | |
|---|---|---|
| CN | 104640906 | 5/2015 |
| CN | 106 754 841 | 5/2017 |
| DE | 950637 | 10/1956 |
| DE | 2840435 | 3/1980 |
| DE | 4301747 | 7/1994 |
| DE | 19644636 | 4/1998 |
| DE | 19844003 | 3/2020 |
| EP | 0172580 | 2/1986 |
| EP | 320032 | 6/1989 |
| EP | 544445 | 6/1993 |
| EP | 632020 | 1/1995 |
| FR | 2456731 | 12/1980 |
| FR | 2836143 | 8/2003 |
| JP | 59-187779 | 10/1984 |
| JP | 60-006191 | 1/1985 |
| JP | S62 201827 | 9/1987 |
| JP | 11-180801 | 7/1999 |
| JP | 2004315511 | 11/2004 |
| JP | 5476119 | 4/2014 |
| JP | 2015216359 | 8/2017 |
| WO | WO 92/08464 | 5/1992 |
| WO | WO 94/017090 | 8/1994 |
| WO | WO 94/29273 | 12/1994 |
| WO | WO 96/02543 | 2/1996 |
| WO | WO 97/24336 | 7/1997 |
| WO | WO 97/29825 | 8/1997 |
| WO | WO 97/45108 | 12/1997 |
| WO | WO 97/45400 | 12/1997 |
| WO | WO 99/62905 | 5/1999 |
| WO | WO 99/43699 | 9/1999 |
| WO | WO 99/55321 | 11/1999 |
| WO | WO 99/55705 | 11/1999 |
| WO | WO 00/01676 | 1/2000 |
| WO | WO 00/18734 | 4/2000 |
| WO | WO 00/35859 | 6/2000 |
| WO | WO 00/41469 | 7/2000 |
| WO | WO 00/59899 | 10/2000 |
| WO | WO 00/71120 | 11/2000 |
| WO | WO 01/10842 | 2/2001 |
| WO | WO 01/56989 | 2/2001 |
| WO | WO 01/14324 | 3/2001 |
| WO | WO 01/14375 | 3/2001 |
| WO | WO 01/44172 | 6/2001 |
| WO | WO 01/72717 | 10/2001 |
| WO | WO 02/62766 | 8/2002 |
| WO | WO 02/66481 | 8/2002 |
| WO | WO 2003/014105 | 2/2003 |
| WO | WO 03/66613 | 8/2003 |
| WO | WO 04/37751 | 5/2004 |
| WO | WO 04/43924 | 5/2004 |
| WO | WO 04/67521 | 8/2004 |
| WO | WO 04/69808 | 8/2004 |
| WO | WO 2004/069833 | 8/2004 |
| WO | WO 2004/069834 | 8/2004 |
| WO | WO 2004/101549 | 11/2004 |
| WO | WO 2004/101564 | 11/2004 |
| WO | WO 2005/021509 | 3/2005 |
| WO | WO 2005/021512 | 3/2005 |
| WO | WO 2005/026123 | 3/2005 |
| WO | WO 2005/026124 | 3/2005 |
| WO | WO 2005/075424 | 8/2005 |
| WO | WO 2005/075468 | 8/2005 |
| WO | WO 2005/085209 | 9/2005 |
| WO | WO 2006/075152 | 7/2006 |
| WO | WO 2006/098684 | 9/2006 |
| WO | WO 2006/135312 | 12/2006 |
| WO | WO 2006/135641 | 12/2006 |
| WO | WO 2007/088996 | 8/2007 |
| WO | WO 2007/093880 | 8/2007 |
| WO | WO 2007/094276 | 8/2007 |
| WO | WO 2007/129962 | 11/2007 |
| WO | WO 2007/129963 | 11/2007 |
| WO | WO 2008/074788 | 6/2008 |
| WO | WO 2008/111598 | 9/2008 |
| WO | WO 2008/139161 | 11/2008 |
| WO | WO 2008/154221 | 12/2008 |
| WO | WO 03/28641 | 4/2009 |
| WO | WO 2009/058076 | 5/2009 |
| WO | WO 2009/100155 | 8/2009 |
| WO | WO 2009/118567 | 10/2009 |
| WO | WO 2010/035820 | 4/2010 |
| WO | WO 2010/126002 | 4/2010 |
| WO | WO 2010/108921 | 9/2010 |
| WO | WO 2011/025565 | 3/2011 |
| WO | WO 2011/113060 | 9/2011 |
| WO | WO 2011/116951 | 9/2011 |
| WO | WO 2011/133179 | 10/2011 |
| WO | WO 2011/160857 | 12/2011 |
| WO | WO 2012/079032 | 6/2012 |
| WO | WO 2012/112919 | 8/2012 |
| WO | WO 2013/036869 | 3/2013 |
| WO | WO 2014/015157 | 1/2014 |
| WO | WO 2015/029445 | 3/2015 |
| WO | WO 2015/160220 | 10/2015 |
| WO | WO 2015/163233 | 10/2015 |
| WO | WO 2016/034642 | 3/2016 |
| WO | WO 2016/049774 | 4/2016 |
| WO | WO 2016/131192 | 8/2016 |
| WO | WO 2017/027984 | 2/2017 |
| WO | WO 2017/044889 | 3/2017 |

OTHER PUBLICATIONS

Written Opinion in International Application No. PCT/US2019/016619, Apr. 22, 2019, pp. 1-9.

European Search Report and Opinion in EP Application No. 19747994.2, Oct. 5, 2021, pp. 1-10.

Chang, J.-H. et al. "Studies on the Packings with Guanido of Affinity Chromatography for the Separation of Urokinase" *Chemical Journal of Chinese Universities*, May 2000, pp. 737-730, vol. 21, No. 5.

Gao, J.-P. et al. "Study on the Packings of Affility Chromatography for the Separation of Urokinase" *Chinese Journal of Chromatography*, Mar. 2000, pp. 1-3, vol. 18, No. 2.

Kumpalume, P et al. "Comparative study of thiophilic functionalised matrices for polyclonal F(ab')$_2$ purification" *Journal of Chromatography A*, 2004, pp. 41-50, vol. 1022.

Hixson, JR, H.F., et al. "Bovine trypsin and thrombin", *Methods in enzymology*, 34, pp. 440-448, 1974.

CHROMATOGRAPHY RESIN HAVING AN ANIONIC EXCHANGE-HYDROPHOBIC MIXED MODE LIGAND

CROSS-REFERENCE TO RELATED APPLICATIONS

This application is a continuation of U.S. application Ser. No. 16/967,429, filed Aug. 5, 2020, now allowed, which is the U.S. national stage application of International Patent Application No. PCT/US2019/016619, filed Feb. 5, 2019, which claims priority from U.S. Ser. No. 62/626,245, filed Feb. 5, 2018.

BACKGROUND

The extraction of immunoglobulins from source liquids, which are primarily mammalian bodily fluids or cell culture harvest, is of value in obtaining the immunoglobulins in a sufficiently concentrated or purified form for diagnostic and therapeutic uses as well as laboratory studies in general. Similarly, purification of other types of proteins and other molecules from biological samples can be of value.

SUMMARY

Chromatography resins comprising chromatography matrices linked to an anionic exchange-hydrophobic mixed mode ligand are provided. In some embodiments, the chromatography resin has the formula:

Chromatography matrix-($X^1$)-L-Ar-($X^2$)-Y or a tautomer or an anionic salt thereof,
wherein:
  $X^1$ is a spacer;
  $X^2$ is $C_1$ to $C_5$ alkyl, $C_3$ or $C_5$ cycloalkyl, or absent;
  L is $NR^8$, O, or S, wherein $R^8$ is hydrogen or $C_1$ to $C_6$ alkyl;
  Ar is a 6- to 10-membered mono or bicyclic ring and is aryl optionally substituted with up to four $C_1$ to $C_3$ unsubstituted alkyl or $C_3$ to $C_6$ branched alkyl; and
  Y is selected from the group consisting of:

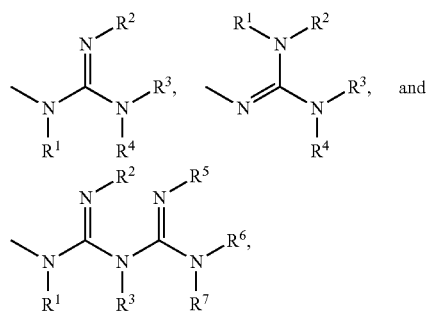

wherein:
  $R^1$, $R^2$, $R^3$, $R^4$, $R^5$, $R^6$, and $R^7$ are each independently hydrogen or $C_1$ to C6 alkyl;

if Y is

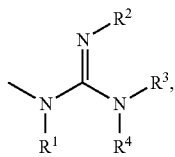

$R^2$ is optionally joined to $R^3$ to form a 4- to 7-membered heterocycle or $R^3$ is optionally joined to $R^4$ to form a 4- to 7-membered heterocycle;
if Y is

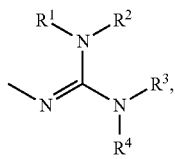

$R^1$ is optionally joined to $R^2$ to form a 4- to 7-membered heterocycle and $R^3$ is optionally joined to $R^4$ to form a 4- to 7-membered heterocycle; and
if Y is

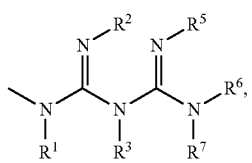

$R^5$ is optionally joined to $R^6$ to form a 4- to 7-membered heterocycle or $R^6$ is optionally joined to $R^7$ to form a 4- to 7-membered heterocycle.

In some embodiments of the chromatography resin:
  $X^1$ is a spacer;
  $X^2$ is $C_1$-$C_3$ alkyl or absent;
  L is $NR^8$, O, or S wherein $R^8$ is hydrogen or $C_1$ to $C_3$ alkyl;
  Ar is phenyl or naphthyl optionally substituted with up to four $C_1$ to $C_3$ unsubstituted alkyl; and
  Y is selected from the group consisting of:

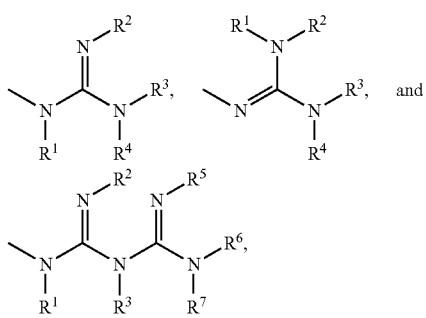

wherein:
  $R^1$, $R^2$, $R^3$, $R^4$, $R^5$, $R^6$, and $R^7$ are each independently hydrogen or $C_1$ to $C_4$ alkyl;

if Y is

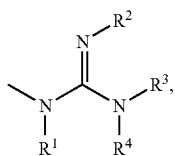

$R^2$ is optionally joined to $R^3$ to form a 4- to 6-membered heterocycle or $R^3$ is optionally joined to $R^4$ to form a 4- to 6-membered heterocycle;
if Y is

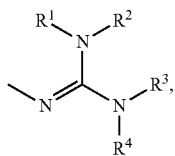

$R^1$ is optionally joined to $R^2$ to form a 4- to 6-membered heterocycle and $R^3$ is optionally joined to $R^4$ to form a 4- to 6-membered heterocycle; and
if Y is

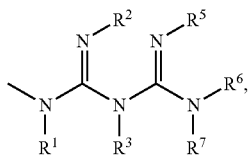

$R^5$ is optionally joined to $R^6$ to form a 4- to 6-membered heterocycle or $R^6$ is optionally joined to $R^7$ to form a 4- to 6-membered heterocycle.

DETAILED DESCRIPTION

A linked chromatography resin that allows for efficient purification of target biomolecules from a sample is provided. Notably, the examples illustrate that the linked chromatography resin is useful for separating monomeric antibodies from antibody aggregates in the sample.

Definitions

Unless otherwise stated, the following terms used in this application, including the specification and claims, have the definitions given below. As used in this specification and the appended claims, the singular forms "a", "an", and "the" include plural referents unless the content clearly dictates otherwise. Definition of standard chemistry terms can be found in reference works, including Carey and Sundberg (2007) "Advanced Organic Chemistry 5th Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

"Antibody" refers to an immunoglobulin, composite (e.g., fusion), or fragmentary form thereof. The term includes but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" also includes composite forms including but not limited to fusion proteins containing an immunoglobulin moiety. "Antibody" also includes antibody fragments such as Fab, F(ab')2, Fv, scFv, Fd, dAb, Fc, whether or not they retain antigen-binding function.

As used herein, the term "alkyl" refers to a straight or branched, saturated, aliphatic radical having between 1-10 carbon atoms. For example, $C_1$-$C_6$ alkyl includes, but is not limited to, methyl, ethyl, propyl, isopropyl, butyl, isobutyl, sec-butyl, tert-butyl, pentyl, isopentyl, and/or hexyl. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two chemical groups together.

As used herein, the term "cycloalkyl" refers to monocyclic alkyl having the number of carbon atoms indicated. Monocyclic rings include, for example, cyclopropyl, cyclobutyl, and cyclopentyl.

As used herein, the term "aryl" refers to a monocyclic or fused bicyclic aromatic ring assembly. For example, aryl can be phenyl, naphthyl, or pyridyl. Aryl groups can optionally be substituted by one, two, three, or four unsubstituted alkyl groups.

As used herein, the term "heterocycle" refers to ring assemblies that include one to three heteroatoms as a ring member. Examples include, but are not limited to, cyclic amines such as azetidino, pyrrolidino, piperidino, pyrazolidino, and imidazolidino. Heterocycles can optionally be substituted by one, two, three, or four alkyl groups.

An "anionic salt" is formed at a basic (e.g., guanidine, amino or alkylamino) group in the ligands. Anionic salts include, but are not limited to, halides, sulfonates, sulfates, carboxylates, phosphates, acetates, citrates and nitrates. Examples of acid-addition salts include, but are not limited to, hydrochloride, hydrobromide, hydroiodide, sulfate, acetate, citrate, and nitrate.

As used herein, the term "spacer" refers to a molecule having 1-30 atoms selected from H, C, N, O and S. The spacer has a neutral charge and can include cyclic groups. The spacer links the chromatographic ligand to the chromatography. The types of bonds used to link the spacer to the chromatography matrix include, but are not limited to, amides, amines, ethers, esters, carbamates, ureas, thioethers, thiocarbamates, thiocarbonate and thioureas. In some embodiments, the bonds used to link the spacer to the chromatography matrix are amines, ethers or amides.

"Biological sample" refers to any composition containing a target molecule of biological origin (a "biomolecule") that is desired to be purified. In some embodiments, the target molecule to be purified is an antibody or a non-antibody protein (e.g., hormones or enzymes).

"Bind-elute mode" refers to an operational approach to chromatography in which the buffer conditions are established so that target molecules and, optionally undesired contaminants, bind to the ligand when the sample is applied to the ligand. Fractionation of the target can be achieved subsequently by changing the conditions such that the target is eluted from the support. In some embodiments, contaminants remain bound following target elution. In some embodiments, contaminants either flow-through or are bound and eluted before elution of the target.

"Flow-through mode" refers to an operational approach to chromatography in which the buffer conditions are established so that the target molecule to be purified flows through the chromatography support comprising the ligand, while at least some sample contaminants are selectively retained, thus achieving their removal from the sample.

Chromatography Ligands

In a first embodiment, a chromatography resin has the formula:

Chromatography matrix-($X^1$)-L-Ar-($X^2$)-Y or a tautomer or an anionic salt thereof,
wherein:
$X^1$ is a spacer;
$X^2$ is $C_1$ to $C_5$ alkyl, $C_3$ or $C_5$ cycloalkyl, or absent;
L is $NR^8$, O, or S, wherein $R^8$ is hydrogen or $C_1$ to $C_6$ alkyl;
Ar is a 6- to 10-membered aryl mono or bicyclic ring optionally substituted with up to four $C_1$ to $C_3$ unsubstituted alkyl or $C_3$ to $C_6$ branched alkyl; and
Y is selected from the group consisting of:

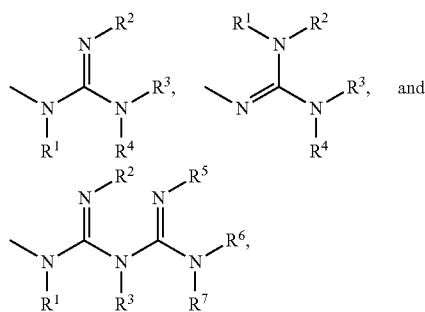

wherein:
$R^1$, $R^2$, $R^3$, $R^4$, $R^5$, $R^6$, and $R^7$ are each independently hydrogen or $C_1$ to $C_6$ alkyl;
if Y is

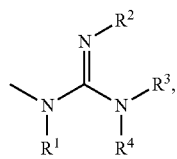

$R^2$ is optionally joined to $R^3$ to form a 4- to 7-membered heterocycle or $R^3$ is optionally joined to $R^4$ to form a 4- to 7-membered heterocycle;
if Y is

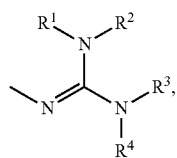

$R^1$ is optionally joined to $R^2$ to form a 4- to 7-membered heterocycle and $R^3$ is optionally joined to $R^4$ to form a 4- to 7-membered heterocycle; and
if Y is

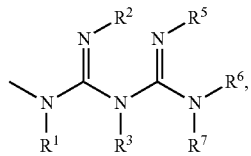

$R^5$ is optionally joined to $R^6$ to form a 4- to 7-membered heterocycle or $R^6$ is optionally joined to $R^7$ to form a 4- to 7-membered heterocycle.

In a first aspect of the first embodiment, $X^2$ is $C_1$-$C_3$ alkyl or absent. Alternatively $X^2$ is $C_1$-$C_2$ alkyl or absent. In yet another alternative, $X^2$ is methyl or absent.

In a second aspect of the first embodiment, L is $NR^8$ or O or $NR^8$ or S. Alternatively, L is $NR^8$ wherein $R^8$ is hydrogen or $C_1$ to $C_3$ alkyl. In yet another alternative, L is NH.

In a third aspect of the first embodiment, Ar is a six-membered aryl optionally substituted with one or two $C_1$ to $C_3$ unsubstituted alkyl. Alternatively, Ar is phenyl optionally substituted with one or two $C_1$ to $C_3$ unsubstituted alkyl. Alternatively, Ar is unsubstituted phenyl.

In a fourth aspect of the first embodiment, Y is

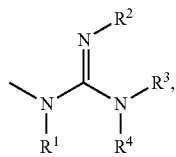

wherein $R^1$-$R^4$ are each independently H or $C_1$-$C_4$ alkyl and $R^2$ is optionally joined to $R^3$ to form a 4- to 7-membered heterocycle or $R^3$ is optionally joined to $R^4$ to form a 4- to 7-membered heterocycle.

Alternatively, Y is

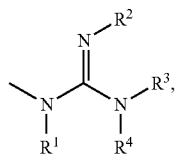

wherein none of $R^1$-$R^4$ form heterocycles and are each independently H or $C_1$-$C_4$ alkyl; each independently H or $C_1$-$C_2$ alkyl; or each H.

In a fifth aspect of the first embodiment, Y is

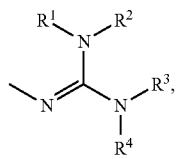

wherein $R^1$-$R^4$ are each independently H or $C_1$-$C_4$ alkyl and $R^1$ is optionally joined to $R^2$ to form a 4- to 7-membered heterocycle and $R^3$ is optionally joined to $R^4$ to form a 4- to 7-membered heterocycle.

Alternatively Y is

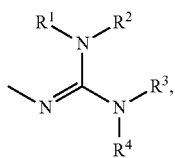

wherein none of $R^1$-$R^4$ form heterocycles and are each independently H or $C_1$-$C_4$ alkyl; each independently H or $C_1$-$C_2$ alkyl; or each H.

In a sixth aspect of the first embodiment, Y is

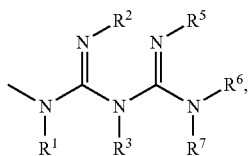

wherein $R^1$-$R^7$ are each independently H or $C_1$-$C_4$ alkyl and wherein $R^5$ is optionally joined to $R^6$ to form a 4- to 7-membered heterocycle or $R^6$ is optionally joined to $R^7$ to form a 4- to 7-membered heterocycle. Alternatively, Y is

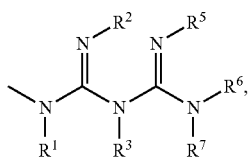

wherein none of $R^1$-$R^7$ form heterocycles and are each independently H or $C_1$-$C_4$ alkyl; each independently H or $C_1$-$C_2$ alkyl; or each H.

In a seventh aspect of the first embodiment, $X^1$ is attached to chromatography matrix via a bond selected from an amide, amine, ether, ester, carbamate, urea, thioether, thiocarbamate, thiocarbonate and thiourea. Alternatively the bond is an amine, ether or amide.

In an eighth aspect of the first embodiment, $X^1$ is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—. $X^1$ is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—.

In a second embodiment, the chromatography resin has the formula:

Chromatography matrix-($X^1$)-L-Ar-($X^2$)-Y or a tautomer or an anionic salt thereof, wherein:
$X^1$ is a spacer;
$X^2$ is $C_1$-$C_3$ alkyl or absent;
L is $NR^8$, O, or S wherein $R^8$ is hydrogen or $C_1$ to $C_3$ alkyl;
Ar is phenyl or naphthyl, optionally substituted with up to four $C_1$ to $C_3$ unsubstituted alkyl; and
Y is selected from the group consisting of:

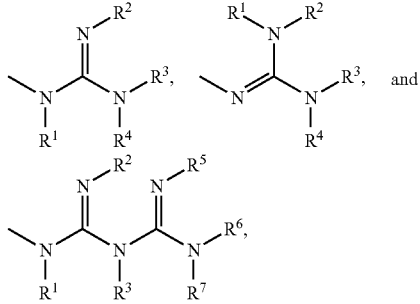

wherein:
$R^1$, $R^2$, $R^3$, $R^4$, $R^5$, $R^6$, and $R^7$ are each independently hydrogen or $C_1$ to C4 alkyl;
if Y is

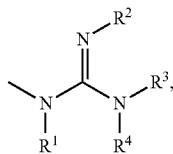

$R^2$ is optionally joined to $R^3$ to form a 4- to 6-membered heterocycle or $R^3$ is optionally joined to $R^4$ to form a 4- to 6-membered heterocycle;
if Y is

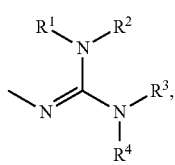

$R^1$ is optionally joined to $R^2$ to form a 4- to 6-membered heterocycle and $R^3$ is optionally joined to $R^4$ to form a 4- to 6-membered heterocycle; and
if Y is

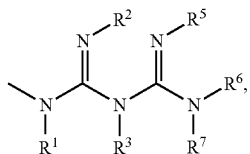

$R^5$ is optionally joined to $R^6$ to form a 4- to 6-membered heterocycle or $R^6$ is optionally joined to $R^7$ to form a 4- to 6-membered heterocycle.

In a first aspect of the second embodiment, $X^2$ is $C_1$-$C_2$ alkyl or absent. In yet another alternative, $X^2$ is methyl or absent.

In a second aspect of the second embodiment, L is $NR^8$ or O or $NR^8$ or S. Alternatively, L is $NR^8$ wherein $R^8$ is hydrogen or $C_1$ to $C_3$ alkyl. In yet another alternative, L is NH.

In a third aspect of the second embodiment, Ar is optionally substituted with one or two $C_1$ to $C_3$ unsubstituted alkyl. Alternatively, Ar is phenyl optionally substituted with one or two $C_1$ to $C_3$ unsubstituted alkyl. Alternatively, Ar is unsubstituted phenyl.

In a fourth aspect of the second embodiment, Y is

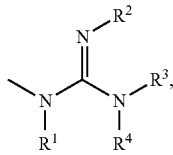

wherein $R^2$ is optionally joined to $R^3$ to form a 4- to 6-membered heterocycle or $R^3$ is optionally joined to R4 to form a 4- to 6-membered heterocycle. Alternatively, Y is

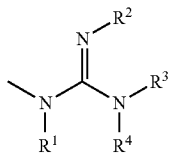

wherein none of $R^1$-$R^4$ form heterocycles and are each independently H or $C_1$-$C_2$ alkyl; or each H.

In a fifth aspect of the second embodiment, Y is

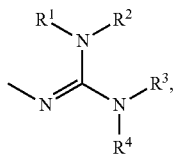

wherein $R^1$ is optionally joined to $R^2$ to form a 4- to 6-membered heterocycle and $R^3$ is optionally joined to $R^4$ to form a 4- to 6-membered heterocycle. Alternatively Y is

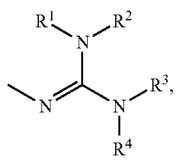

wherein none of $R^1$-$R^4$ form heterocycles and are each independently H or $C_1$-$C_2$ alkyl; or each H.

In a sixth aspect of the second embodiment, Y is

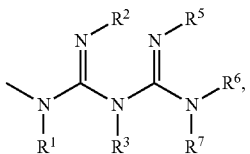

wherein $R^5$ is optionally joined to $R^6$ to form a 4- to 6-membered heterocycle or $R^6$ is optionally joined to $R^7$ to form a 4- to 6-membered heterocycle. Alternatively, Y is

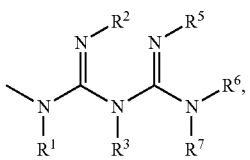

wherein none of $R^1$-$R^7$ form heterocycles and are each independently H or $C_1$-$C_2$ alkyl; or each H.

In a seventh aspect of the second embodiment, $X^1$ is attached to chromatography matrix via a bond selected from an amide, amine, ether, ester, carbamate, urea, thioether, thiocarbamate, thiocarbonate and thiourea. Alternatively the bond is an amine, ether or amide.

In an eighth aspect of the second embodiment, $X^1$ is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$-OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—. Alternatively, $X^1$ is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—

In a third embodiment, a chromatography resin has the formula:

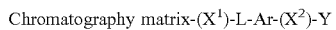

Chromatography matrix-($X^1$)-L-Ar-($X^2$)-Y or a tautomer or an anionic salt thereof,
wherein:
$X^1$ is a is selected from the group consisting of —O13 $CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—CH2—$CH_2$—$CH_2$—$CH_2$—O—$CH_2$—CH(OH)—$CH_2$, and —CO—NH—C(CH3)$_2$—CO—;

$X^2$ is —$CH_2$— or absent;

L is $NR^8$ wherein $R^8$ is hydrogen or —$CH_3$;

Ar is phenyl optionally substituted with one or two $C_1$ to $C_2$ unsubstituted alkyl; and Y is selected from the group consisting of:

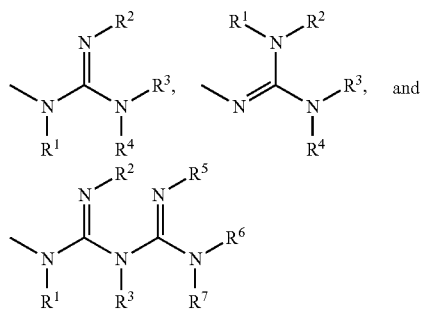

wherein:
R$^1$, R$^2$, R$^3$, R$^4$, R$^5$, R$^6$, and R$^7$ are each independently hydrogen or C$_1$ to C$_3$ alkyl.

In a first aspect of the third embodiment, L is NH.

In a second aspect of the third embodiment, Ar unsubstituted phenyl.

In a third aspect of the third embodiment, Y is

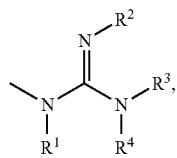

wherein R$^1$-R$^4$ are each independently H or C$_1$-C$_3$ alkyl; or each independently H or C$_1$-C$_2$ alkyl; or each H.

In a fourth aspect of the third embodiment, Y is

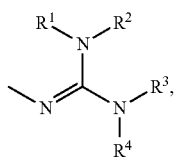

wherein R$^1$-R$^4$ are each independently H or C$_1$-C$_2$ alkyl; or each H.

In a fifth aspect of the third embodiment, Y is

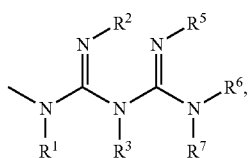

wherein R$^1$-R$^7$ are each independently H or C$_1$-C$_2$ alkyl; or each H.

In a sixth aspect of the third embodiment, X$^1$ is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, and —O—CH$_2$—CH(CH$_2$—OH)—(O—CH$_2$—CH(OH)—CH$_2$)$_2$—.

In a fourth embodiment, chromatography matrix-(X$^1$)-L-Ar-(X$^2$)-Y is any one of the chromatography resin structures listed in the last column of Table 1.

TABLE 1

| Number | Ligand Name | Ligand Structure | Structure of Chromatography Resin (spheres represent matrix and spacer X$^1$) |
|---|---|---|---|
| 1 | 1-(4-aminophenyl)guanidine | | |
| 2 | 1-(4-aminobenzyl)guanidine | | |
| 3 | 1-(4-aminophenyl-propyl)guanidine | | |
| 4 | 1-(4-aminophenyl-butyl)guanidine | | |

TABLE 1-continued

| Number | Ligand Name | Ligand Structure | Structure of Chromatography Resin (spheres represent matrix and spacer X¹) |
|---|---|---|---|
| 5 | 1-(4-aminophenyl-pentyl) guanidine | | |
| 6 | 1-(4-aminophenyl-cyclopropyl) guanidine | | |
| 7a | 1-(4-aminophenyl-cyclobutyl) guanidine | | |
| 7b | | | |
| 8a | 1-(4-aminophenyl-cyclopentyl) guanidine | | |
| 8b | | | |

TABLE 1-continued

| Number | Ligand Name | Ligand Structure | Structure of Chromatography Resin (spheres represent matrix and spacer $X^1$) |
|---|---|---|---|
| 9 | 3-(4-aminophenyl)-1,1-dimethyl-guanidine | | |
| 10 | 3-(4-aminobenzyl)-1,1-dimethyl-guanidine | | |
| 11 | 1-(4-aminophenyl-ethyl)guanidine | | |
| 12 | 1-(amino(4-aminobenzyl)amino)methyl-guanidine | | |
| 13 | 4-(((1,3-dimethyl-imidazolidin-2-ylidene)amino)methyl)aniline | | |
| 14 | 2-(4-aminobenzyl)-1,1,3,3-tetramethyl-guanidine | | |
| 15 | 2-(4-aminophenyl)-1,1,3,3-tetramethyl-guanidine | | |
| 16 | 1-((6-amino-naphthalen-2-yl)methyl)guanidine | | |

TABLE 1-continued

| Number | Ligand Name | Ligand Structure | Structure of Chromatography Resin (spheres represent matrix and spacer $X^1$) |
|---|---|---|---|
| 17 | N-(4-aminobenzyl)azetidine-1-carboximidamide | 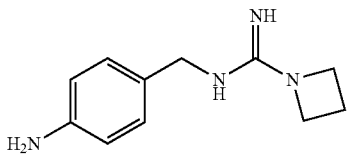 [SMILES: N=C(NCc1ccc(N)cc1)N1CCC1] | 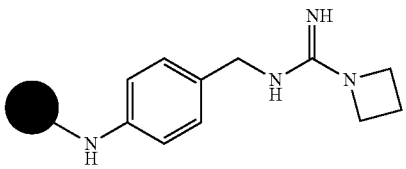 [SMILES: CNc1ccc(CNC(=N)N2CCC2)cc1] |
| 18 | 4-(((di(pyrrolidin-1-yl)methyl)amino)methyl)aniline | 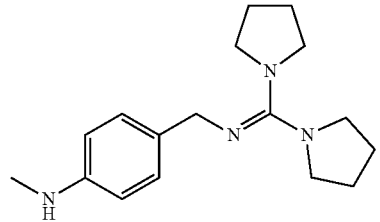 [SMILES: CNc1ccc(CN=C(N2CCCC2)N2CCCC2)cc1] | 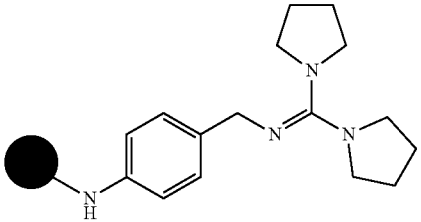 [SMILES: CNc1ccc(CN=C(N2CCCC2)N2CCCC2)cc1] |
| 19 | 1-(4-aminobenzyl)-3-(imidazolidin-2-ylidene)guanidine | 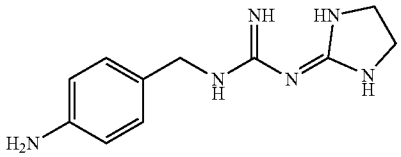 [SMILES: N=C(N=C1NCCN1)NCc1ccc(N)cc1] | 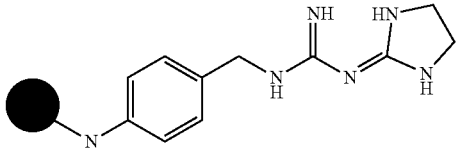 |
| 20 | N-(N-(4-aminobenzyl)carbamidoyl)azetidine-1-carboximidamide | 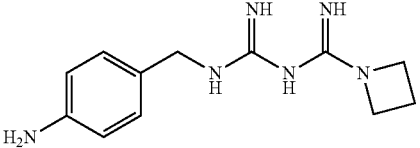 [SMILES: N=C(NCc1ccc(N)cc1)NC(=N)N1CCC1] | 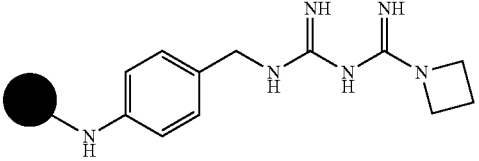 [SMILES: CNc1ccc(CNC(=N)NC(=N)N2CCC2)cc1] |
| 21 | 1-(2-aminobenzyl)guanidine | 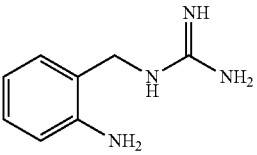 [SMILES: N=C(N)NCc1ccccc1N] | 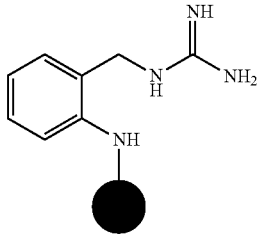 |
| 22 | 1-(3-aminobenzyl)guanidine | 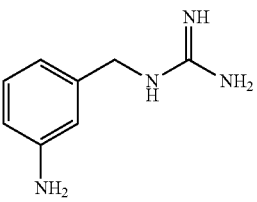 | 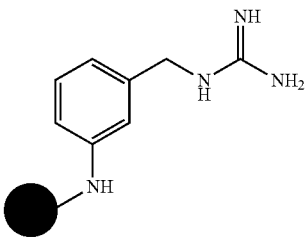 |

In some embodiments, the salt is hydrochloride or sulfate.

The chromatography matrix is a polymer that is functionalized so that a bond can be formed to the spacer, $X^1$. Preferably, the polymer is a hydrophilic polymer. The polymer is insoluble in water. Suitable polymers are polyhydroxy polymers, e.g. based on polysaccharides, such as agarose (e.g., Sepharose and Superose beads from GE Healthcare and Biogel A from Bio-Rad), dextran (e.g., Sephadex from GE Healthcare), cellulose, starch, pullulan, and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinyl alcohols and polymers based on styrenes and divinylbenzenes, and copolymers in which two or more of the monomers corresponding to the above-mentioned polymers are included. Suitable synthetic polymers include, but are not limited to, Fractogel from Toso-Haas, POROS media from ThermoFisher Scientific, Bio-Gel P and Macro Prep from Bio-Rad, HEMA and Separon from TESSEK, and Hyper D and Trisacryl media from Pall. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to OH, or by hydrophilization of the final polymer, e.g. by adsorption of suitable compounds, such as hydrophilic polymers. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Cross-linking agents are also of use in many embodiments, and when present can in some embodiments constitute a mole ratio of from about 0.1 to about 0.7 relative to total monomer. Examples of crosslinking agents are dihydroxyethylenebisacrylamide, di allyltartardiamide, tri-allyl citric triamide, ethylene diacrylate, bisacrylylcystamine, N,N'-methylenebisacrylamide, and piperazine diacrylamide.

In some embodiments, the matrix is an UNOsphere™ support, a polymer produced from water-soluble hydrophilic monomers (Bio-Rad, Hercules, Calif.).

The chromatography matrix can be in the form of a particle, chips, a membrane, or a monolith, i.e., a single block, pellet, or slab of material. Preferably, the chromatography matrix is porous. Particles when used as matrices can be spheres or beads and are either smooth-surfaced or with a rough or textured surface. In some cases, some of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is about 25 microns to about 150 microns. Disclosures of exemplary matrices and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666.

The ligands are linked to the chromatography matrix via the spacer $X^1$. Linkage to the chromatography matrix will depend on the chromatography matrix used and the chemical group to be linked to the chromatography matrix. Ligands can be linked to the chromatography matrix by performing a reaction between the ligand and a functional group on the chromatography matrix. For chromatography matrices that do not have a suitable functional group, the chromatography matrix is reacted with a suitable activating reagent to create a suitable functional group to which the ligand can be attached. Reductive amination, epoxide chemistry or azalactone chemistry are examples of chemistries acting on aldehyde, epoxide, or azalactone functional groups, respectively. For example, a chromatography matrix functionalized with an aldehyde or a ketone group can be used to link the chromatography matrix to an amine group in the ligand. In some embodiments, the chromatography matrix comprises a diol, which is converted to an aldehyde, e.g., by conversion with $NaIO_4$. A primary amine of the ligand can be linked to the created aldehyde on the chromatography matrix by a reductive amination reaction by the scheme below. In this scheme, the spacer X is —O—$CH_2$—$CH_2$—. In this and other synthetic schemes in this disclosure, the box represents the matrix and all coupling chemistry is shown separately.

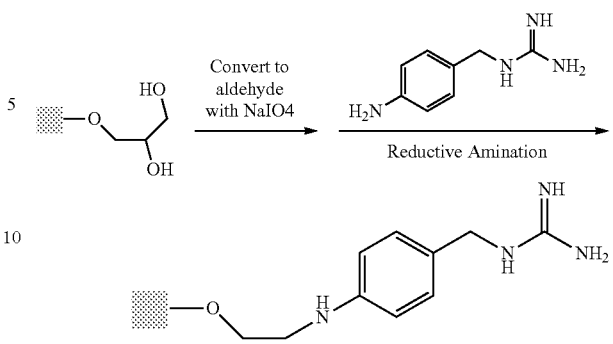

In some embodiments, the chromatography matrix comprises an epoxide group and a primary amine in the ligand is linked to the epoxide group via epoxide chemistry by the scheme below. In this scheme, the spacer X is —O—$CH_2$—CH(OH)—$CH_2$—.

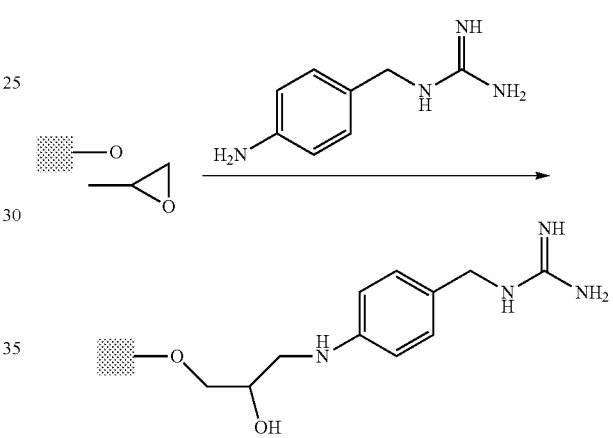

In some embodiments, the chromatography matrix comprises an azlactone ring and a primary amine in the ligand is linked to the azlactone ring by the scheme below. In this scheme, the spacer X is —CO—NH—C(CH3)$_2$—CO—.

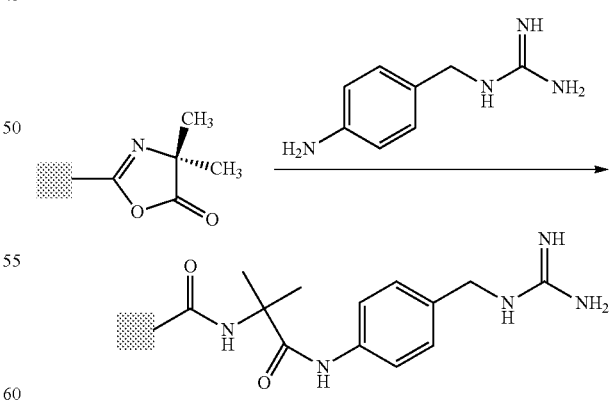

In some embodiments, the chromatography matrix comprises a diol and a primary amine is linked to an —OH group by activating the resin with two activating reagents, allylglydicylether (AGE) and bromine, by the scheme below. In this scheme, the spacer X is —O—$CH_2$—CH($CH_2$—OH)—(O—$CH_2$—CH(OH)—$CH_2$)$_2$—.

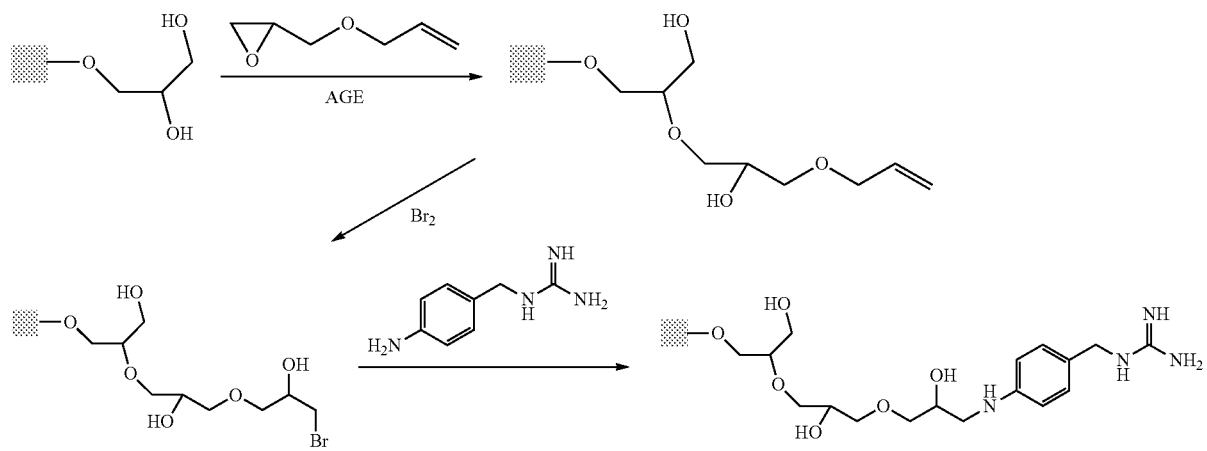

In certain embodiments, the chromatography matrix comprises an —OH group and a primary amine is linked to the —OH group by activating the resin with epichlorohydrin by the scheme below. In this scheme, the spacer X is —O—CH$_2$—CH(OH)—CH$_2$—.

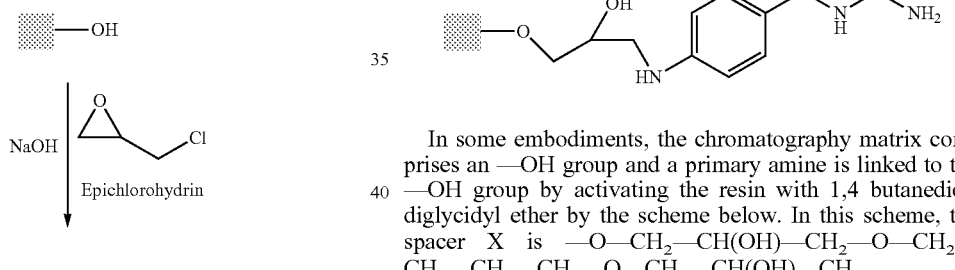

In some embodiments, the chromatography matrix comprises an —OH group and a primary amine is linked to the —OH group by activating the resin with 1,4 butanediol-diglycidyl ether by the scheme below. In this scheme, the spacer X is —O—CH$_2$—CH(OH)—CH$_2$—O—CH$_2$—CH$_2$—CH$_2$—CH$_2$—O—CH$_2$—CH(OH)—CH$_2$—.

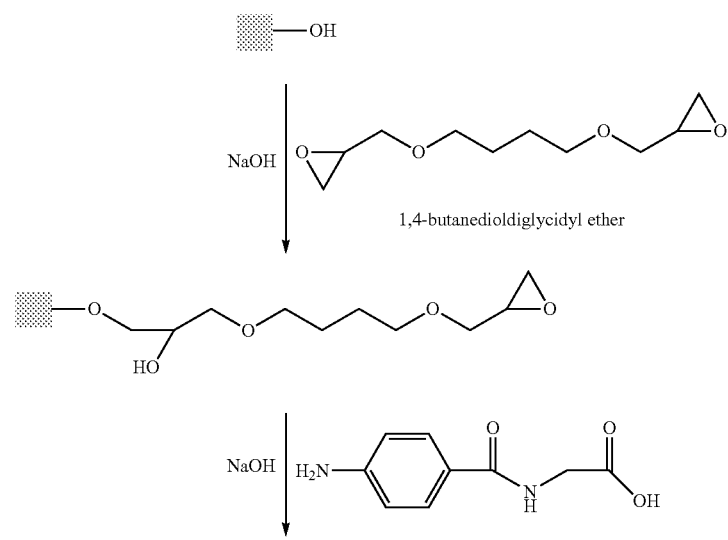

-continued

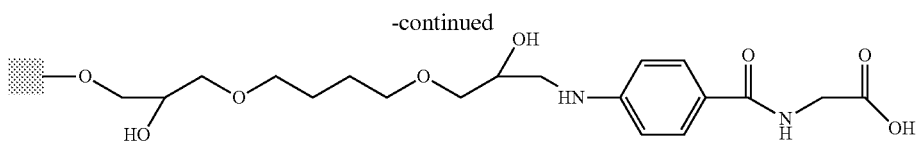

Other activating reagents include, but are not limited to, epibromohydrin, bis-epoxides such as; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides.

Other spacers can include, but are not limited to, —O—$CH_2$—, —O—$CH_2$—$CH_2$—$CH_2$—, —O—$CH_2$—$CH_2$—$CH_2$—$CH_2$—, —O—$CH_2$—$CH_2$—CH($CH_2$—OH)—(O—$CH_2$—$CH_2$—CH(OH)—$CH_2$)$_2$—, and —O—$CH_2$—$CH_2$—CH(OH)—$CH_2$—$CH_2$—.

The chromatography matrix can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, a column can range in diameter from 1 cm to 1 m, and in height from 1 cm to 30 cm or more.

Depending on the pH of the chromatography mobile phase buffer, any nitrogen in the ligand can be protonated and; thus, can carry a positive charge.

Methods

Also provided are methods of purifying a target biomolecule. In an embodiment, the method comprises contacting a sample comprising the biomolecule to a chromatography resin , thereby separating the biomolecule from a contaminant. The resulting purified biomolecule is subsequently collected. In some embodiments, the target biomolecule is a monomeric antibody and the method comprises purifying the monomeric antibody from aggregated antibodies in the sample.

The chromatographic resins are useful for purifying target molecules using anionic exchange (i.e., where the ligand is positively charged) and hydrophobic mixed mode chromatography. The conditions can be adjusted so as to run the chromatography in bind-elute mode or flow-through mode.

Protein preparations to which the methods can be applied can include unpurified or partially purified proteins, including but not limited to, antibodies (e.g. IgG, IgM) and non-antibody proteins from natural, synthetic, or recombinant sources. Unpurified protein preparations, for example, can come from various sources including, but not limited to, plasma, serum, ascites fluid, milk, plant extracts, bacterial lysates, yeast lysates, or conditioned cell culture media. Partially purified protein preparations can come from unpurified preparations that have been processed by at least one chromatography, precipitation, other fractionation step, or any combination of the foregoing. In some embodiments, the chromatography step or steps employ any method, including but not limited to size exclusion, affinity, anion exchange, cation exchange, protein A affinity, hydrophobic interaction, immobilized metal affinity chromatography, or hydroxyapatite chromatography. The precipitation step or steps can include salt or polyethylene glycol (PEG) precipitation, or precipitation with organic acids, organic bases, or other agents. Other fractionation steps can include but are not limited to crystallization, liquid:liquid partitioning, or membrane filtration.

As will be appreciated in the art, load, wash and elution conditions for use in the mixed mode chromatography will depend on the specific chromatography matrix/ligand used.

In some bind-elute mode embodiments, loading (i.e., binding the antibodies or non-antibody protein to the chromatography resin), and optionally washing, is performed at a pH above 7, e.g., between 7-8 or 7-9. Some exemplary bind-elute conditions are:

binding condition: 0-1000 mM NaCl or 100-300 mM NaCl, pH 6.5-8.5 in an appropriate buffer (e.g., Tris, Bis-Tris or phosphate);

elution condition: 1-1000 mM NaCl or 0-150 mM NaCl, pH 3-8.5 or 3.0-5.0, using an appropriate buffer having sodium acetate, citrate, arginine, or glycine.

Optionally, the chromatography resin can be washed under conditions such that some components of the sample are removed from the chromatography resin but the target biomolecules remain immobilized on the resin. In some embodiments, the target biomolecule is subsequently eluted by lowering the salt concentration and/or reducing the pH of the solution in contact with the resin.

Alternatively, the sample can be applied in flow through mode in which some components of the sample are immobilized to the chromatography resin but the target biomolecules flow through (i.e., flow passed) the chromatography resin, and is collected. Some exemplary flow through conditions are 0-150 mM NaCl, pH 4.0-8.0; appropriate buffers can include, e.g., 2-(N-morpholino)ethanesulfonic acid (IVIES), Bis-Tris, sodium acetate or citrate-phosphate.

EXAMPLES

The following examples are provided by way of illustration only and not by way of limitation. Those of skill in the art will readily recognize a variety of non-critical parameters that could be changed or modified to yield essentially the same or similar results.

Example 1—Preparation of Chromatography Resins having the ligands of Table 2

TABLE 2

| Number from Table 1 | Structure of Chromatography Resin (Spheres represent Chromatography matrix and spacer $X^1$) |
|---|---|
| 1 | |

TABLE 2-continued

| Number from Table 1 | Structure of Chromatography Resin (Spheres represent Chromatography matrix and spacer X¹) |
|---|---|
| 2 | ●—NH—C6H4—CH2—NH—C(=NH)—NH2 |
| 11 | ●—NH—C6H4—CH2CH2—NH—C(=NH)—NH2 |
| 12 | ●—NH—C6H4—CH2—NH—C(=NH)—NH—C(=NH)—NH2 |
| 13 | ●—NH—C6H4—CH2—N=C(imidazolidine with N-methyl) |
| 14 | ●—NH—C6H4—CH2—N=C(N(CH3)2)2 |
| 15 | ●—NH—C6H4—NH—C(=N—N(CH3)2)—N(CH3)— |

For each of the ligands in Table 2, UNOSPHERE® Diol (20 mL), a copolymer of 3-allyloxy-1,2-propanediol and vinyl pyrrolidinone, crosslinked with N,N'-methylenebisacrylamide and with a diol density of 200-300 µmol/mL, was used in the form of spherical beads. For each ligand, beads were suspended in 20 mL of either 0.1M sodium acetate or water. Sodium periodate was added to a concentration within the range of 50 to 100 mM, and the resulting mixtures were incubated at room temperature (approximately 70° F. (21° C.)) for 3-24 hours. The reactions resulted in conversion of the diol groups to aldehyde groups in the range of 150-250 µmol/mL. Each of the resulting aldehyde-functionalized beads was transferred to a 20-mL column where each resin was washed with 100 mL of water.

For each ligand, twenty milliliters of aldehyde-functionalized beads was then suspended in 20 ml of 0.20M sodium phosphate containing 0.6 g of N-(4-aminophenyl)guanidine at pH 7.0. After these mixtures were incubated (shaking, 200 rpm) at room temperature for 15 minutes, 200 mg NaBH3CN was then added and the reactions were allowed to continue for 3-20 hours. The ligand concentration in each reaction was determined to be in the range of 25-200 mM. At the end of the reactions, each resin was transferred to a 20 ml column, washed with 3 CV of water followed by 1-2 CV of 0.1N HCl, and then washed with 5 CV water. The ligand density for all the resins was in the range of 25-100 µmol/ml.

Example 2—Purification of Antibodies Using the resins of Example 1 and Flow Through Mode Each of the resins listed in Table 2 (generated as described above) are packed into a 7 mm (i.d.)×5.5 cm column and is equilibrated with 20 mM sodium acetate containing 75 mM NaCl at pH 4.5. 750 µl of a 2.0 mg/ml solution of a monoclonal IgG antibody containing 15-20% aggregated antibodies is applied to the column at a flow rate of 2 ml/minute. The antibody flows through each of the columns. To remove contaminants that bind to each resin, each column is washed in a 10 ml gradient of equilibration buffer to elution buffer with 20 mM sodium acetate at pH 4.5, followed by a 10 ml isocratic elution with elution buffer. The collected antibody in the flow-through fractions of each column is analyzed by size exclusion high performance liquid chromatography (HPLC-SEC) to determine the content of aggregated antibody. No antibody aggregates are detected in the antibody flow-through fractions for each column.

Example 3—Purification of Antibodies Using the Resins of Example 1 and Bind-Elute Mode (Gradient Elution)

Each of the resins listed in Table 2 is packed into a 7 mm (i.d.)×5.5 cm column and equilibrated with 20 mM Tris-HCl buffer containing 300 mM NaCl, pH 8.5. 500 µl of 6.0 mg/ml solution of a monoclonal IgG antibody containing 5-10% aggregated antibodies is applied to each column at a flow rate of 2 ml/minute. For each column, the antibody is eluted in a 10 ml gradient of equilibration buffer to elution buffer with 20 mM sodium acetate containing 150 mM NaCl at pH 4.5, followed by a 30 ml isocratic elution with elution buffer. The collected antibody elution fractions of each column are analyzed by size exclusion high performance liquid chromatography (HPLC-SEC) to determine the content of aggregated antibody in the elution fractions. No antibody aggregates are detected in the antibody elution fractions of any of the columns.

Example 4—Purification of Antibodies Using the Resins of Example 1 and Bind-Elute Mode (Step Elution and Gradient Elution)

Each resin in Table 2 was tested in bind-elute mode for the ability to remove aggregates from impure antibody solutions and/or for the ability of a pure antibody (i.e., no aggregates) to bind to the resin. Various antibodies were tested.

Materials

1. Chromatography resins listed in Table 2.
2. Samples containing one of the following monoclonal antibodies (mAbs). The amount of mAb in the samples was determined by Bradford assay using bovine IgG as a standard.

a. Humanized anti-vascular endothelial growth factor monoclonal antibody (mAb1)—about 15 mg of mAb1 in 7 mL crude Chinese hamster ovary (CHO) cell harvest (or about 2 mg/mL). The crude CHO cell harvest contained 5-10% aggregated mAb1.
b. Anti-human epidermal growth factor receptor 2 monoclonal antibody (mAb2)—about 15 mg of mAb2 in 5 mL crude Chinese hamster ovary (CHO) cell harvest (or about 3 mg/mL). The crude CHO cell harvest contained 5-10% aggregated mAb2.
c. Purified mAb3—about 15 mg in 3 ml binding buffer (or about 5 mg/mL).
d. Purified mAb4—about 15 mg in 3 ml binding buffer (or about 5 mg/mL).
3. Columns: 7 mm (i.d.)×5.5 cm.
4. Binding/wash buffer:
   a. 1×PBS—10 mM phosphate, 137 mM sodium chloride (NaCl), and 2.7 mM potassium chloride, pH 7.2 or 7.8.
   b. Modified 1×PBS (higher NaCl concentration)—10 mM phosphate, 300 mM sodium chloride (NaCl), and 2.7 mM potassium chloride, pH 7.2
5. Elution buffer: 50 mM sodium acetate (NaOAc), pH 5.0 or 5.4 or 100 mM glycine, pH 3.
6. Stripping buffer: 1 N sodium hydroxide (NaOH).

Methods: For each resin in Table 2, the resin was packed into a column and equilibrated with the binding/wash buffer listed in Table 3. Samples containing mAb (see Table 3 for the sample applied to each resin) were applied to the columns and the columns were washed with binding/wash buffer. For step elution, the monomeric or purified mAb was eluted with 10 column volumes (CV) of elution buffer. For gradient elution (i.e., resin 2 tested with mAb1), the antibody was eluted with a 15 CV gradient of binding/wash buffer to elution buffer, followed by 5 CV isocratic elution with elution buffer. All the columns were cleaned or stripped with stripping buffer after the mAb was eluted.

The collected antibody elution fractions of each column were analyzed by size exclusion high performance liquid chromatography (HPLC-SEC) to determine the percent aggregate content of antibody in the elution fractions. The percent monomer content for the samples was determined by subtracting the percent aggregate content from 100% and is listed in Table 3.

In Table 3, "~" symbolizes "about".

TABLE 3

| Number from Table 1 | Antibody | Binding and Wash buffer | Elution Conditions | Monomer content (%) |
|---|---|---|---|---|
| 1 | mAb1 | 1× PBS, pH 7.2 | Step elution: 10 CV 50 mM NaOAc, pH 5.4 | ~99 |
| 2 | mAb1 | 1× PBS, pH 7.2 | Step elution: 10 CV 50 mM NaOAc, pH 5.4 | ~97 |
|  | mAb1 | 1× PBS, pH 7.8 | Gradient elution: 0-100% 50 mM NaOAc, Ph 5.0, 15 CV, then hold for 5 CV | ~97 |
|  | mAb2 | 1× PBS, pH 7.8 | Step elution: 10 CV 50 mM NaOAc, pH 5.0 | ~97 |
|  | Purified mAb3 | 1× PBS, pH 7.8 | Step elution: 10 CV 50 mM NaOAc, pH 5.0 | None eluted with step elution; Eluted with 100 mM glycine pH 3 (monomer content ~75%) |
|  | Purified mAb4 | 1× PBS, pH 7.8 | Step elution: 10 CV 50 mM NaOAc, pH 5.0 | ~97 |
| 11 | mAb1 | 1× PBS, pH 7.2 | Step elution: 10 CV 50 mM NaOAc, pH 5.4 | Monomer content not determined, assumed the same as Resin 2 (~97) |
| 12 | Purified mAb4 | 1× PBS, pH 7.2 | Step elution: 10 CV 50 mM NaOAc, pH 5.4 | 0 |
|  |  | Modified 1× PBS, pH 7.2, 300 mM NaCl | Step elution: 10 CV 50 mM NaOAc, pH 5.4 | Eluted in both the flow through and eluate; monomer content in combined FT and eluate ~100 |
| 13 | mAb1 | 1× PBS, pH 7.2 | Step elution: 10 CV 50 mM NaOAc, pH 5.4 | ~97 |
| 14 | mAb1 | 1× PBS, pH 7.2 | Step elution: 10 CV 50 mM NaOAc, pH 5.4 | Eluted in both the FT and eluate; monomer content in combined FT and eluate ~94 |
| 15 | mAb1 | 1× PBS, pH 7.2 | Step elution: 10 CV 50 mM NaOAc, pH 5.4 | Eluted in both the FT and eluate; monomer content in combined FT and eluate ~94 |

Results: The results in Table 3 show that, by varying the binding and elution conditions, any of the resins can be used to purify antibodies (i.e., to remove aggregates). For example, monomeric mAb1 was bound to Resins 1, 2, and 11 with 1×PBS, pH 7.2 or pH 7.8 and more than 97% monomeric mAb1 was eluted by step elution with 50 mM NaOAc, pH 5.4 or pH 5.0. For resin 2, gradient elution (i.e., 0-100% 50 mM NaOAc, pH 5.0) was also used to purify mAb1: the results show that more than 97% monomeric mAb1 was eluted. Additionally, for resins 14 and 15, monomeric mAb1 was collected in the flow through with 1×PBS, pH 7.2 binding buffer and 50 mM NaOAc, pH 5.4 elution buffer.

All patents, patent applications, and other published reference materials cited in this specification are hereby incorporated herein by reference in their entirety.

ADDITIONAL DISCLOSURE AND CLAIMABLE SUBJECT MATTER

Item 1. A chromatography resin having the formula:

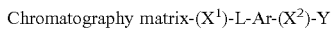

Chromatography matrix-($X^1$)-L-Ar-($X^2$)-Y or a tautomer or an anionic salt thereof,
wherein:
  $X^1$ is a spacer;
  $X^2$ is $C_1$ to $C_5$ alkyl, $C_3$ or $C_5$ cycloalkyl, or absent;
  L is $NR^8$, O, or S wherein $R^8$ is hydrogen or $C_1$ to $C_6$ alkyl;
  Ar is a 6- to 10-membered aryl mono or bicyclic ring optionally substituted with up to four $C_1$ to $C_3$ unsubstituted alkyl or $C_3$ to $C_6$ branched alkyl; and
  Y is selected from the group consisting of:

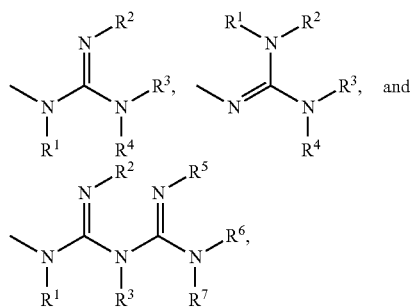

wherein:
  $R^1$, $R^2$, $R^3$, $R^4$, $R^5$, $R^6$, and $R_7$ are each independently hydrogen or $C_1$ to $C_6$ alkyl;
  if Y is

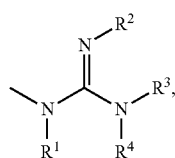

$R^2$ is optionally joined to $R^3$ to form a 4- to 7-membered heterocycle or $R^3$ is optionally joined to $R^4$ to form a 4- to 7-membered heterocycle;

if Y is

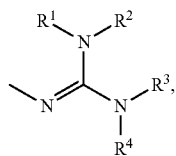

$R^1$ is optionally joined to $R^2$ to form a 4- to 7-membered heterocycle and $R^3$ is optionally joined to $R^4$ to form a 4- to 7-membered heterocycle; and
if Y is

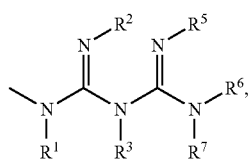

$R^5$ is optionally joined to $R^6$ to form a 4- to 7-membered heterocycle or $R^6$ is optionally joined to $R^7$ to form a 4- to 7-membered heterocycle.

Item 2. The chromatography resin of item 1,
wherein:
  $X^2$ is $C_1$-$C_3$ alkyl or absent;
  L is $NR^8$, O, or S wherein $R^8$ is hydrogen or $C_1$ to $C_3$ alkyl;
  Ar is phenyl or naphthyl optionally substituted with up to four $C_1$ to $C_3$ unsubstituted alkyl; and
  Y is selected from the group consisting of:

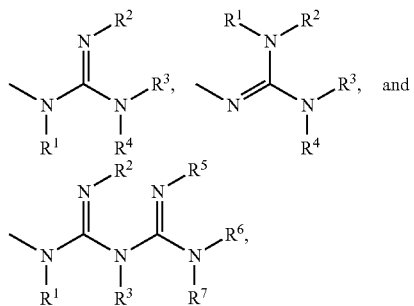

wherein:
  $R^1$, $R^2$, $R^3$, $R^4$, $R^5$, $R^6$, and $R_7$ are each independently hydrogen or $C_1$ to $C_4$ alkyl;
  if Y is

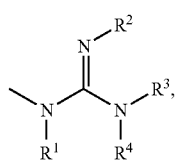

$R^2$ is optionally joined to $R^3$ to form a 4- to 6-membered heterocycle or $R^3$ is optionally joined to $R^4$ to form a 4- to 6-membered heterocycle;

if Y is

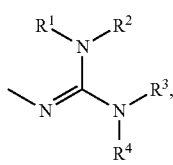

$R^1$ is optionally joined to $R^2$ to form a 4- to 6-membered heterocycle and $R^3$ is optionally joined to $R^4$ to form a 4- to 6-membered heterocycle; and if Y is

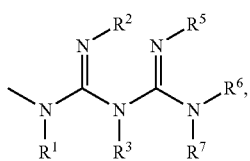

$R^5$ is optionally joined to $R^6$ to form a 4- to 6-membered heterocycle or $R^6$ is optionally joined to $R^7$ to form a 4- to 6-membered heterocycle.

Item 3. The chromatography resin of item 2, wherein:
$X^1$ is a is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH$_2$—CH(CH$_2$—OH)—(O—CH$_2$—CH(OH)—CH$_2$)$_2$—, —O—CH$_2$—CH$_2$—CH(CH$_2$—OH)—(O—CH$_2$—CH$_2$—CH(OH)—CH$_2$)$_2$—, CH(OH)—CH$_2$—, —O—CH$_2$—CH$_2$—CH(OH)—CH$_2$—CH$_2$—, —O—CH$_2$—CH(OH)—CH$_2$—O—CH$_2$—CH$_2$—CH$_2$—CH$_2$—O—CH$_2$—CH(OH)—CH$_2$—, and —CO—NH—C(CH$_3$)$_2$—CO—;

$X^2$ is —CH$_2$— or absent;

L is NR$^8$ wherein R$^8$ is hydrogen or —CH$_3$;

Ar is phenyl optionally substituted with one or two C$_1$ to C$_2$ unsubstituted alkyl; and Y is selected from the group consisting of:

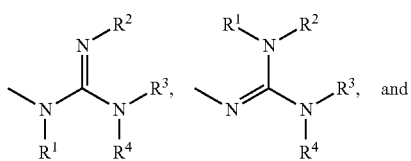

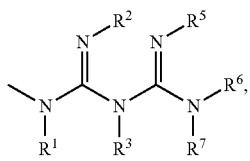

wherein:
$R^1$, $R^2$, $R^3$, $R^4$, $R^5$, $R^6$, and $R^7$ are each independently hydrogen or C$_1$ to C$_3$ alkyl.

Item 4. The chromatography resin of item 1 or 2, wherein Y is

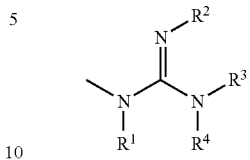

and $R^2$ is joined to $R^3$ to form a 4- or 5-membered heterocycle.

Item 5. The chromatography resin of item 1 or 2, wherein Y is

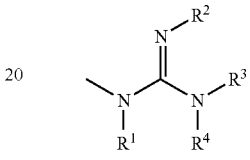

and $R^3$ is joined to $R^4$ to form a 4- to 6-membered heterocycle.

Item 6. The chromatography resin of item 1 or 2, wherein Y is

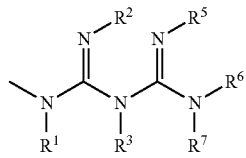

and $R^5$ is joined to $R^6$ to form a 4- or 5-membered heterocycle or $R^6$ is joined to $R^7$ to form a 4- or 5-membered heterocycle.

Item 7. The chromatography resin of any one of items 1-6, wherein $R^1$-$R^7$ are each independently hydrogen, C$_1$ or C$_2$ alkyl.

Item 8. The chromatography resin of item 7, wherein $R^1$-$R^7$ are each independently hydrogen or —CH$_3$.

Item 9. The chromatography resin any previous item, wherein $X^1$ is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, and —O—CH$_2$—CH(CH$_2$—OH)—(O—CH$_2$—CH(OH)—CH$_2$)$_2$—.

Item 10. The chromatography resin of any previous item, wherein Ar is unsubstituted.

Item 11. The chromatography resin of any one of items 1-10, wherein if Ar is phenyl, chromatography matrix-($X^1$)-L- is at a para or meta position relative to ($X^2$)-Y.

Item 12. The chromatography resin of any one of items 1-11, wherein chromatography matrix-($X^1$)-L-Ar-($X^2$)-Y is any one of the structures in the right-most column of Table 1.

Item 13. The chromatography resin of any one of items 1-12, wherein the anionic salt is hydrochloride or sulfate.

Item 14. A chromatography resin prepared by reacting any one of the ligands of Table 1 with a chromatography matrix by any one of reductive amination, epoxide chemistry, or azalactone chemistry.

Item 15. The chromatography resin of item 14, wherein the chromatography matrix comprises an aldehyde group and any one of the ligands of Table 1 is reacted with the chromatography matrix by reductive amination.

Item 16. The chromatography resin of item 14, wherein the chromatography matrix comprises an epoxide group and any one of the ligands of Table 1 is reacted with the chromatography matrix by epoxide chemistry.

Item 17. The chromatography resin of any one of items 14-16 wherein prior to reacting the chromatography matrix with the ligand the chromatography matrix is reacted with allylglydicylether and bromine; 1,4-butanedioldiglycidyl; or epichlorohydrin.

Item 18. The chromatography resin of item 17, wherein the chromatography matrix comprises an —OH group and it is reacted with allylglydicylether and bromine.

Item 19. A method of purifying a biomolecule, the method comprising:
contacting a sample comprising the biomolecule to a chromatography resin of any one of items 1-18, thereby separating the biomolecule from a contaminant; and collecting a purified biomolecule.

Item 20. The method of item 19, wherein the purified biomolecule is a protein.

Item 21. The method of item 20, wherein the protein is an antibody.

Item 22. The method of any one of items 19-21, wherein the sample comprises a monomeric antibody and antibody aggregates, the method comprises separating the monomeric antibody from the antibody aggregates, and the purified biomolecule comprises the monomeric antibody.

Item 23. The method of item 22, wherein the contacting step comprises immobilizing the monomeric antibody to the chromatography matrix and the collecting step comprises eluting the monomeric antibody from the chromatography matrix.

Item 24. The method of item 23, wherein the monomeric antibody is eluted with a pH gradient of a buffer in contact with the ligand from about 7-9 to about 3-6.

Item 25. The method of item 22, wherein the contacting step comprises flowing the monomeric antibody through the chromatography matrix and the collecting step comprises collecting the monomeric antibody in the flow through.

The invention claimed is:

1. A chromatography configuration comprising a packed column, fluidized column, expanded-bed column, monolith or porous membrane comprising a chromatography resin having the formula:

Chromatography matrix-($X^1$)-L-Ar-($X^2$)-Y or a tautomer or an anionic salt thereof,
wherein:
$X^1$ is a spacer;
$X^2$ is $C_1$ to $C_5$ alkyl, $C_3$ or $C_5$ cycloalkyl;
L is $NR^8$, O, or S wherein $R^8$ is hydrogen or $C_1$ to $C_6$ alkyl;
Ar is a 6- to 10-membered aryl mono or bicyclic ring optionally substituted with up to four $C_1$ to $C_3$ unsubstituted alkyl or $C_3$ to $C_6$ branched alkyl; and
Y is selected from the group consisting of:

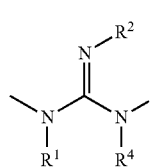 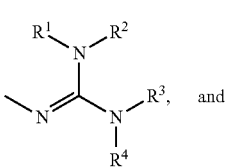 and

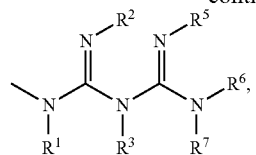

wherein:
$R^1$, $R^2$, $R^3$, $R^4$, $R^5$, $R^6$, and $R^7$ are each independently hydrogen or $C_1$ to $C_6$ alkyl;
if Y is

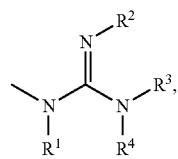

$R^2$ is optionally joined to $R^3$ to form a 4- to 7-membered heterocycle or $R^3$ is optionally joined to $R^4$ to form a 4- to 7-membered heterocycle;
if Y is

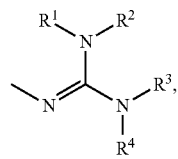

$R^1$ is optionally joined to $R^2$ to form a 4- to 7-membered heterocycle and $R^3$ is optionally joined to $R^4$ to form a 4- to 7-membered heterocycle; and
if Y is

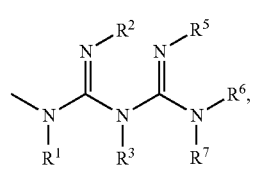

$R^5$ is optionally joined to $R^6$ to form a 4- to 7-membered heterocycle or $R^6$ is optionally joined to $R^7$ to form a 4- to 7-membered heterocycle.

2. The chromatography configuration of claim 1, wherein:
$X^2$ is $C_1$-$C_3$ alkyl;
L is $NR^8$, O, or S wherein $R^8$ is hydrogen or $C_1$ to $C_3$ alkyl;
Ar is phenyl or naphthyl optionally substituted with up to four $C_1$ to $C_3$ unsubstituted alkyl; and
Y is selected from the group consisting of:

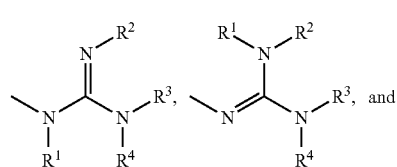

-continued

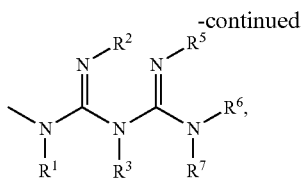

wherein:
R¹, R², R³, R⁴, R⁵, R⁶, and R⁷ are each independently hydrogen or $C_1$ to $C_4$ alkyl;
if Y is

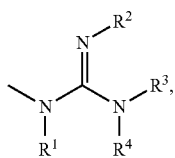

R² is optionally joined to R³ to form a 4- to 6-membered heterocycle or R³ is optionally joined to R⁴ to form a 4- to 6-membered heterocycle;
if Y is

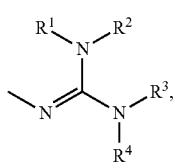

R¹ is optionally joined to R² to form a 4- to 6-membered heterocycle and R³ is optionally joined to R⁴ to form a 4- to 6-membered heterocycle; and
if Y is

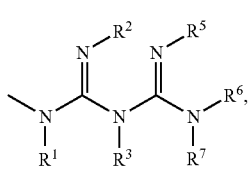

R⁵ is optionally joined to R⁶ to form a 4- to 6-membered heterocycle or R⁶ is optionally joined to R⁷ to form a 4- to 6-membered heterocycle.

3. The chromatography configuration of claim 1, wherein:
X¹ is selected from the group consisting of —O—CH₂—, —O—CH₂—CH₂—, —O—CH₂—CH₂—CH₂—, —O—CH₂—CH₂—CH₂—CH₂—, —O—CH₂—CH(CH₂—OH)—(O—CH₂—CH(OH)—CH₂)₂—, —O—CH₂—CH₂—CH(CH₂—OH)—(O—CH₂—CH(OH)—CH₂)₂—, —O—CH₂—CH(OH)—CH₂—, —O—CH₂—CH₂—CH(OH)—CH₂—CH₂—, —O—CH₂—CH(OH)—CH₂—O—CH2—CH₂—CH₂—CH₂—O—CH₂—CH(OH)—CH₂—, and —CO—NH—C(CH3)₂—CO—;
X² is —CH₂—;
L is NR⁸ wherein R⁸ is hydrogen or —CH₃;
Ar is phenyl optionally substituted with one or two $C_1$ to $C_2$ unsubstituted alkyl; and Y is selected from the group consisting of:

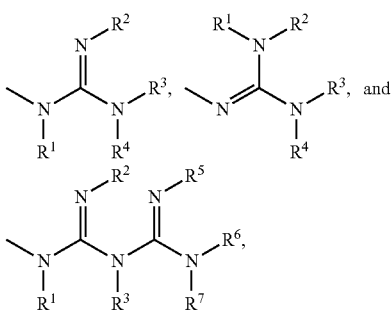

wherein:
R¹, R², R³, R⁴, R⁵, R⁶, and R⁷ are each independently hydrogen or $C_1$ to $C_3$ alkyl.

4. The chromatography configuration of claim 1, wherein R¹-R⁷ are each independently hydrogen, $C_1$ or $C_2$ alkyl.

5. The chromatography configuration of claim 4, wherein R¹-R⁷ are each independently hydrogen or —CH₃.

6. The chromatography configuration of claim 1, wherein X¹ is selected from the group consisting of —O—CH₂—, —O—CH₂—CH₂—, —O—CH₂—CH₂—CH₂—, —O—CH₂—CH₂—CH₂—CH₂—, and —O—CH₂—CH(CH₂—OH)—(O—CH₂—CH(OH)—CH₂)₂—.

7. The chromatography configuration of claim 1, wherein Ar is unsubstituted.

8. The chromatography configuration of claim 1, wherein if Ar is phenyl, chromatography matrix-(X¹)-L- is at a para or meta position relative to (X²)-Y.

9. The chromatography configuration of claim 1, wherein chromatography matrix-X¹-L-Ar-X²-Y is any one of the following structures:

| Number | Structure of Chromatography Resin (spheres represent matrix and spacer X¹) |
|---|---|
| 2 | |
| 3 | |
| 4 | |
| 5 | |

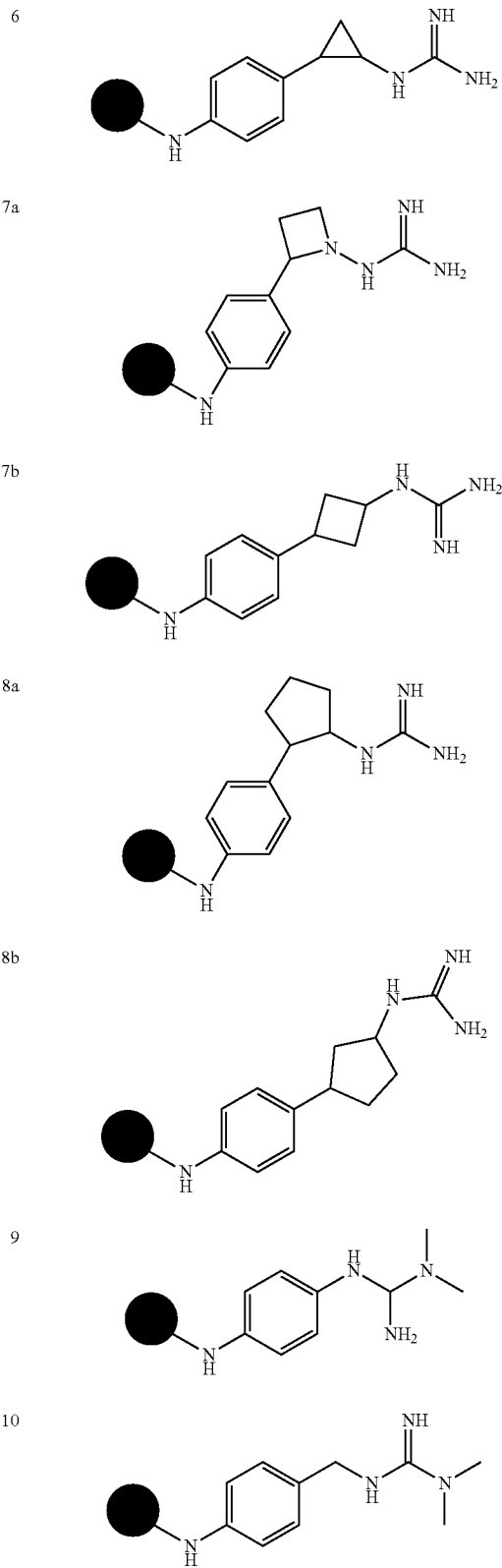
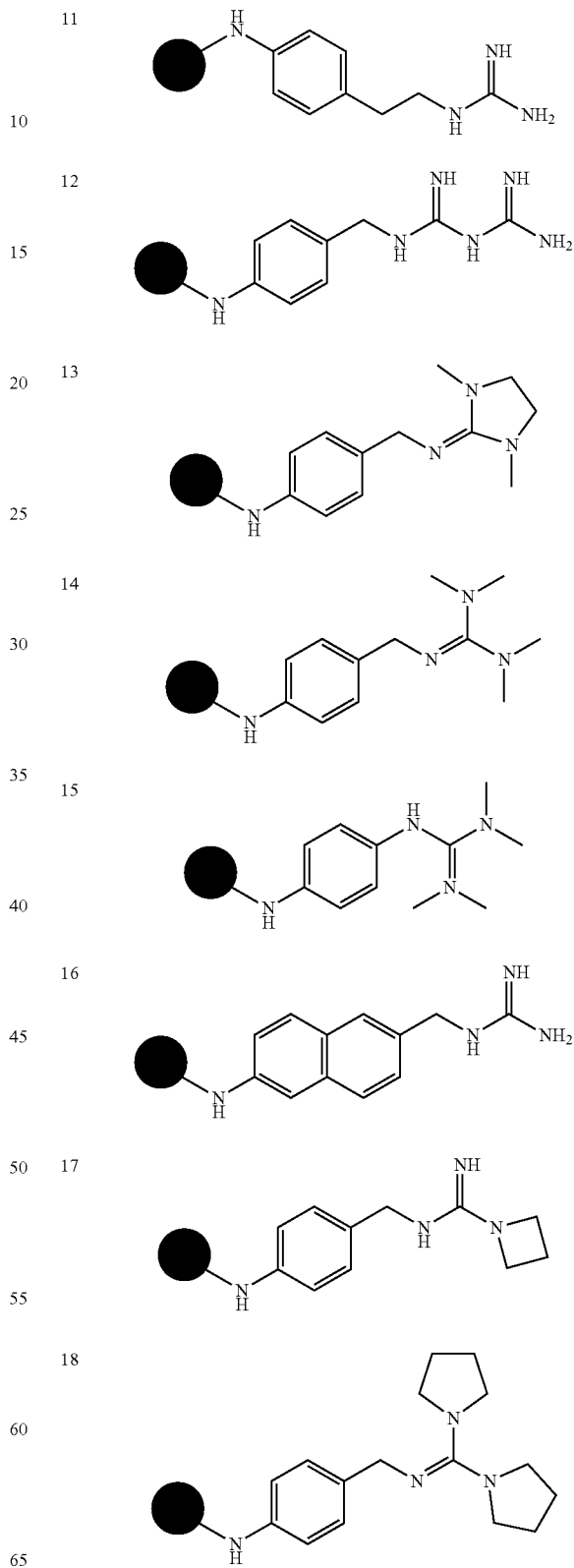

-continued

| Number | Structure of Chromatography Resin (spheres represent matrix and spacer $X^1$) |
|---|---|
| 19 | |
| 20 | |
| 21 | |
| 22 | |

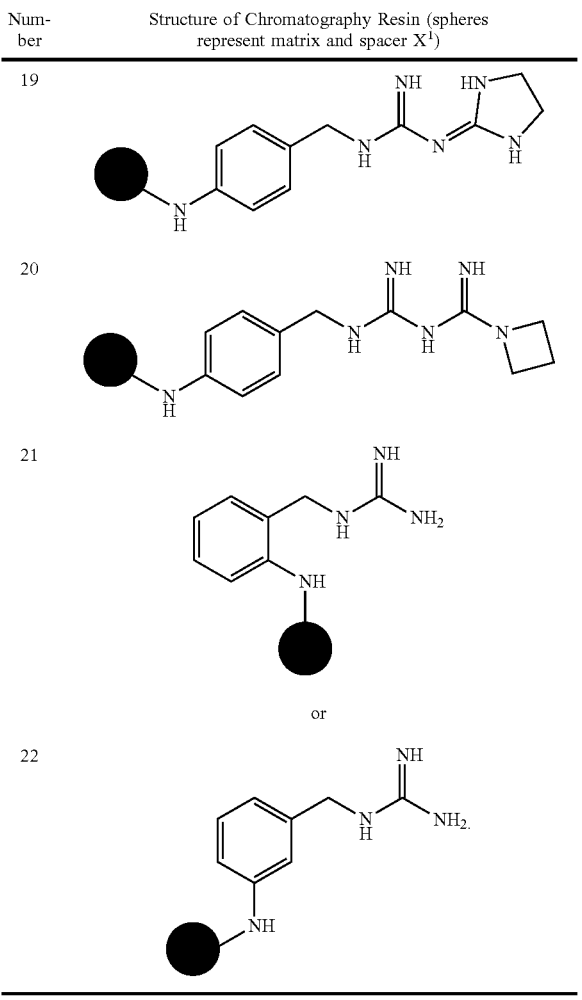

10. The chromatography configuration of claim 1, wherein the anionic salt is hydrochloride or sulfate.

11. A method of purifying a biomolecule, the method comprising:
    contacting a sample comprising the biomolecule to a chromatography configuration of claim 1, thereby separating the biomolecule from a contaminant; and
    collecting a purified biomolecule.

12. The method of claim 11, wherein the purified biomolecule is a protein.

13. The method of claim 12, wherein the protein is an antibody.

14. The method of claim 11, wherein the sample comprises a monomeric antibody and antibody aggregates, the method comprises separating the monomeric antibody from the antibody aggregates, and the purified biomolecule comprises the monomeric antibody.

15. The method of claim 14, wherein the contacting step comprises immobilizing the monomeric antibody to the chromatography matrix and the collecting step comprises eluting the monomeric antibody from the chromatography matrix.

16. The method of claim 15, wherein the monomeric antibody is eluted with a pH gradient of a buffer in contact with the ligand from about 7-9 to about 3-6.

17. The method of claim 14, wherein the contacting step comprises flowing the monomeric antibody through the chromatography matrix and the collecting step comprises collecting the monomeric antibody in the flow through.

18. A chromatography configuration comprising a chromatography resin having the formula:

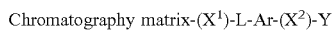

or a tautomer or an anionic salt thereof,
wherein:
   $X^1$ is a spacer;
   $X^2$ is $C_1$ to $C_5$ alkyl, $C_3$ or $C_5$ cycloalkyl or is absent;
   L is $NR^8$, O, or S wherein $R^8$ is hydrogen or $C_1$ to $C_6$ alkyl;
   Ar is a 6- to 10-membered aryl mono or bicyclic ring optionally substituted with up to four $C_1$ to $C_3$ unsubstituted alkyl or $C_3$ to $C_6$ branched alkyl; and
   Y is selected from the group consisting of:

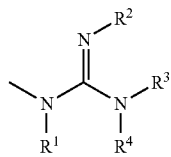

wherein $R^1$ and $R^4$ are each independently hydrogen or $C_1$ to $C_6$ alkyl and $R^2$ is joined to $R^3$ to form a 4- or 5-membered heterocycle;

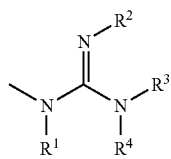

wherein $R^1$ and $R^2$ are each independently hydrogen or $C_1$ to $C_6$ alkyl and $R^3$ is joined to $R^4$ to form a 4- to 6-membered heterocycle; and

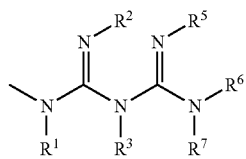

wherein $R^1$, $R^2$, $R^3$, and $R^4$ are each independently hydrogen or $C_1$ to $C_6$ alkyl and $R^5$ is joined to $R^6$ to form a 4- or 5-membered heterocycle or $R^1$, $R^2$, $R^3$, $R^4$, and $R^5$ are each independently hydrogen or $C_1$ to $C_6$ alkyl $R^6$ is joined to $R^7$ to form a 4- or 5-membered heterocycle.

19. The chromatography configuration of claim 18, wherein Y is

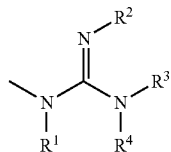

wherein $R^1$ and $R^2$ are each independently hydrogen or $C_1$ to $C_6$ alkyl and $R^3$ is joined to $R^4$ to form a 4- to 6-membered heterocycle.

20. The chromatography configuration of claim 18, wherein Y is

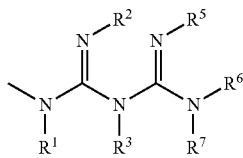

wherein $R^1$, $R^2$, $R^3$, $R^4$, and $R^7$ are each independently hydrogen or $C_1$ to $C_6$ alkyl and $R^5$ is joined to $R^6$ to form a 4- or 5-membered heterocycle or $R^1$, $R^2$, $R^3$, $R^4$, and $R^5$ are each independently hydrogen or $C_1$ to $C_6$ alkyl and $R^6$ is joined to $R^7$ to form a 4- or 5-membered heterocycle.

21. The chromatography configuration of claim 18, wherein Y is

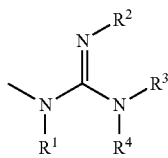

wherein $R^1$ and $R^4$ are each independently hydrogen or $C_2$ to $C_6$ alkyl and $R^2$ is joined to R3 to form a 4- or 5-membered heterocycle.

22. A method of purifying a biomolecule, the method comprising:
contacting a sample comprising the biomolecule to a chromatography configuration of claim 18, thereby separating the biomolecule from a contaminant; and
collecting a purified biomolecule.

23. The method of claim 22, wherein the purified biomolecule is a protein.

24. The method of claim 23, wherein the protein is an antibody.

25. The method of claim 22, wherein the sample comprises a monomeric antibody and antibody aggregates, the method comprises separating the monomeric antibody from the antibody aggregates, and the purified biomolecule comprises the monomeric antibody.

26. The method of claim 25, wherein the contacting step comprises immobilizing the monomeric antibody to the chromatography matrix and the collecting step comprises eluting the monomeric antibody from the chromatography matrix.

27. The method of claim 26, wherein the monomeric antibody is eluted with a pH gradient of a buffer in contact with the ligand from about 7-9 to about 3-6.

28. The method of claim 25, wherein the contacting step comprises flowing the monomeric antibody through the chromatography matrix and the collecting step comprises collecting the monomeric antibody in the flow through.

\* \* \* \* \*